United States Patent
Böhm et al.

(10) Patent No.: US 6,610,090 B1
(45) Date of Patent: Aug. 26, 2003

(54) HEIGHT-ADJUSTABLE VERTEBRAL IMPLANT

(75) Inventors: Heinrich Böhm, Weimar (DE); Thomas Busch, Bad Blankenburg (DE); Erich Orschler, Kirchenpingarten (DE)

(73) Assignee: Königsee Implantate und Instrumente zur Ostheosynthese GmbH, Königsce (DE)

( * ) Notice: Subject to any disclaimer, the term of this patent is extended or adjusted under 35 U.S.C. 154(b) by 0 days.

(21) Appl. No.: 09/601,157

(22) PCT Filed: May 29, 1998

(86) PCT No.: PCT/EP98/03245
§ 371 (c)(1),
(2), (4) Date: Dec. 14, 2000

(87) PCT Pub. No.: WO99/38460
PCT Pub. Date: Aug. 5, 1999

(30) Foreign Application Priority Data

Jan. 30, 1998 (DE) .......................... 198 03 700

(51) Int. Cl.⁷ .................................. A61F 2/44
(52) U.S. Cl. ................... 623/17.11; 623/17.16
(58) Field of Search ............ 623/17.11, 17.15, 623/17.16, 17.13; 606/61

(56) References Cited

U.S. PATENT DOCUMENTS

| | | | |
|---|---|---|---|
| 4,401,112 A | * | 8/1983 | Rezaian |
| 4,657,550 A | * | 4/1987 | Daher |
| 5,290,312 A | * | 3/1994 | Kojimoto et al. |
| 5,405,391 A | * | 4/1995 | Hednerson et al. |
| 5,571,192 A | * | 11/1996 | Schönhöffer |
| 5,782,832 A | * | 7/1998 | Larsen et al. |
| 5,989,290 A | * | 11/1999 | Biedermann et al. |
| 6,193,756 B1 | * | 2/2001 | Studer et al. ............ 623/17.15 |
| 6,200,348 B1 | * | 3/2001 | Biedermann et al. .... 623/17.11 |

FOREIGN PATENT DOCUMENTS

| | | | |
|---|---|---|---|
| DE | 195 00 170 | * | 2/1996 |
| DE | 296 16 778 | * | 1/1998 |
| WO | WO 92/01428 | * | 2/1992 |

\* cited by examiner

*Primary Examiner*—Ralph A. Lewis
(74) *Attorney, Agent, or Firm*—Friedrich Kueffner

(57) ABSTRACT

The invention relates to a height-adjustable vertebral implant comprising a first essentially U-shaped cage which has recesses or holes and vertebral support surfaces which are formed at the cage. The first cage is encompassed and guided telescopically by a second, outer U-shaped cage, with the legs of the inner and outer cages being formed in such a manner that a continuous lateral opening is obtained. One end face each of the cages has upper and lower angular, tongue-like vertebral support surfaces as well as tooth-like locking projections which extend in the longitudinal direction. The inner and outer cages can be fixed in a pregiven end position relative to one another.

8 Claims, 3 Drawing Sheets

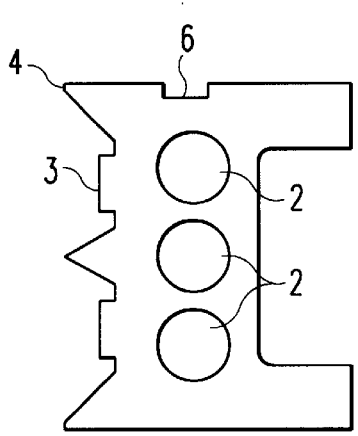
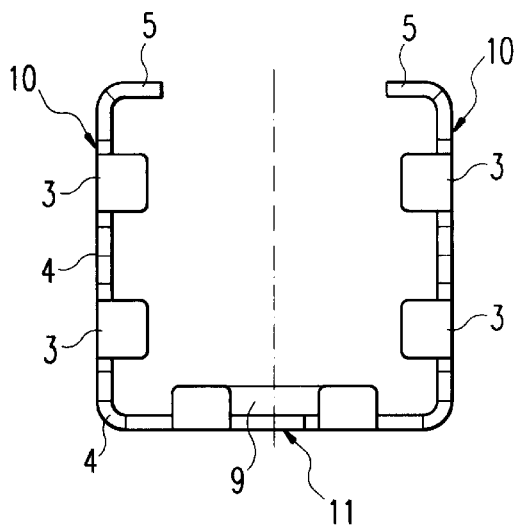
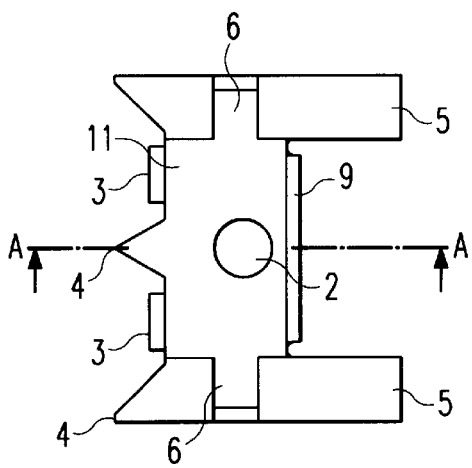
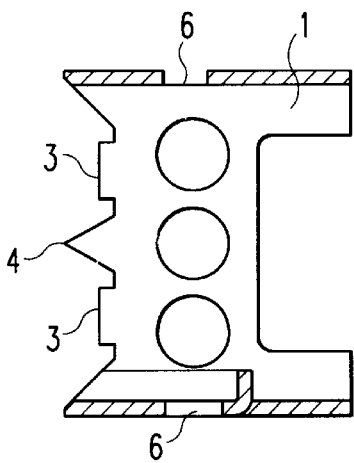
Fig. 1a
Fig. 1c
Fig. 1b
Fig. 1d

HEIGHT-ADJUSTABLE VERTEBRAL IMPLANT

BACKGROUND OF THE INVENTION

1. Field of the Invention

The invention relates to a height-adjustable vertebral implants, comprising a first essentially you-shaped cage with recesses or holes and cardboard support services which are formed at said cage.

2. Discussion of the Related Art

From DE 43 28 062 A1 a supporting bar with laterally arranged slide-on implant bodies is known. In order to enable a sliding-on action, the implant bodies are provided with a lateral groove and with a surface structure in the form of a toothing, respectively. The surface structure secures the surfaces of the implant bodies to one another and, in addition, maintains the position with respect to the vertebral body or bodies, respectively.

From EP 0 302 719 a U-shaped implant is known wherein openings are provided which serve to introduce bone cement. Further opening may be provided for accommodating a screw in order to secure the implant immediately in the vertebra. Carbon fibre reinforced synthetic material is specified for the shown implant.

The implant according to EP 0 268 115 A1 comprises a cylinder jacket element with a plurality of rhomboidal recesses. A ring at the upper and lower end of the cylinder jacket element prevents an undesired excessively deep penetration of the implant into the vertebra. An additionally provided base plate serves the same purpose. The cylinder jacket element is closed and has no further openings apart from the rhomboidal openings for the introduction of bone cement, so that in this case, too, there are difficulties in the surgical handling with disadvantages in the injection of bone cement.

DE 196 15 938 A1 discloses a vertebral column supporting device for carrying out an intersomatic arthrodesis. The supporting device consists of titanium, has a plane and elongated shape with an expansion in its central area. The edges with the exception of the central area are provided with a saw tooth profile. The shape of the presented supporting device is similar to that of an open ring, with the supporting device being adaptable with respect to its diameter to various applications by means of bending up the end portions of the supporting device.

A height-adjustable vertebral substitution with a sleeve and with a first abutment body with is displaceable in an axial direction or a second abutment, respectively, is known from DE 44 09 392 A1. For displacing the abutment bodies relative to each other, a threaded means is provided. A similar principle is shown in DE 44 23 257 A1.

An adjustability via a thread is also mentioned in DE 196 19 101 A1, wherein tooth-shaped recesses are provided at the ends of the sleeve portions of the vertebral substitution, in order to realise a radial locking relative to the vertebrae. The cylindrical portions of the vertebral substitution have a plurality of recesses in order to improve the growing through with body material. The transplanting of the vertebra substitution according to DE 195 10 101 A1, however, is extremely critical because a corresponding spreading of the vertebrae must be done. In addition, the metal mass of the known implant is too great with the associated, disadvantageous post-operative consequences.

DE 195 09 317 A1 shows an implant for transplanting between vertebral bodies of the vertebral column, with two end plate-shaped implant portions being provided which interact with an intermediate central implant portion which is rotatably connected with the end plate-shaped implant portions. The shown implant portions are formed as tubular sleeve or end ring, respectively. Bone cement can be introduced via provided openings. However, these openings are suited optimally for the insertion of bone cement only if they are brought to coincide, which, however, with the chosen adjusting principle is difficult.

With respect to adjustability, reference is also made to U.S. Pat. No. 5,236,460 which shows a telescopic arrangement of an implant, wherein a curing material can be introduced into the telescopic space by means of a special tool. On the other hand, EP 0 637 439 A1 shows an implant with a wedge drive for height adjustment. In addition, locking teeth can be pivoted outwards in order to claw the implant between the vertebrae after its placement.

On the basis of the above, it is therefore the object of the invention to provide an advanced, height-adjustable vertebral implant which has an excellent stability with a minimum amount of material, which can be handled particularly easily under surgical conditions, and which comprises optimised opening for the introduction of bone cement while simultaneously being height-adjustable.

SUMMARY OF THE INVENTION

The object of the invention is solved by means of the device of the aforementioned kind in that the first cage is an inner cage which is encompassed and telescopically guided by a second, outer U-shaped cage, with the legs of the inner and outer cages being aligned in such a manner that a continuous lateral opening is obtained, one each of the end faces of the cages comprises upper and lower, angular, tongue-like vertebral supporting surfaces as well as tooth-like blocking projections which extend in the longitudinal direction, and in that the inner and outer cages can be fixed in a pre-given end position relative to one another, with suitable embodiments and developments being disclosed also.

The basic idea of the invention is to have an inner cage which in its longitudinal direction is open and which is essentially U-shaped encompassed by an outer cage which is essentially configured in the same manner, with both cages being telescopically guided relative to one another. In addition, locking in at least two end positions is possible. The height adjustment is made either by means of a special tool to be inserted from the open side of the cages, or by utilising a provided toothing in cooperation with an adjusting screw.

It is to be noted that the term U-shaped can also cover a polygon shape, a semi-circular or circular cylindrical shape or the like, i.e. that which matters for the inventive cages is the possibility of the telescopic guidance inside one another, and the mutual support of the side walls, whereby it is ensured that a continuous, lateral opening is obtained.

In addition to the securing in the end position, preferably by means of screws, metallic tongues are provided which can engage claw-like with corresponding recesses so that the stability of the arrangement in increased, in spite of the open U-shape for the introduction of bone cement. Angular, tongue-like vertebral support surfaces as well as tooth-like locking projections extending in the longitudinal direction prevent a rotation of the vertebral implant after the transplantation and an undesired excessively deep penetration of the implant into the neighbouring vertebrae after the surgery.

When being used, at first the inner cage is inserted into the outer cage, i.e. the implant with the inner part being inserted in this manner is positioned between the vertebrae, while subsequently the outwardly-directed movement of the inner part into its end position or the relative movement of the cages, respectively, is carried out. In the end position, securing of the inner part relative to the outer part, i.e. of the cages relative to each other, can be carried out by means of a corresponding screw, with a latching or craw-like engagement of the metal tongue which is preferably provided in the outer part being possible in cooperation with the corresponding recess in the inner part.

In the embodiment with an elongated hole in the inner cage and a toothing provided at same, there is the possibility of a continuous height adjustment by inserting a tool via the open side of the U-shaped cages.

As explained above, the invention comprises a first inner cage which is encompassed and guided by an outer U-shaped cage. The legs of the inner and outer cages are aligned in such a manner that a lateral continuous hole is obtained. This lateral continuous hole faces the surgeon during the operation and enables both the insertion of a tool for making the explained height adjustment or locking, respectively, and the optimum introduction of bone cement.

One each of the end faces of the cages comprises upper and lower, angular, tongue-like vertebral support surfaces as well as tooth-like locking projections which extend in the longitudinal direction. With the embodiment as a metallic implant, these vertebral supporting surfaces or locking projections, respectively, can be manufactured in a simple manner by punching and bending so that the manufacturing costs are kept low.

In order to increase the stability of the vertebral implant the legs of the inner and outer cages comprise at their leg ends one each inwardly directed curved portion. Thereby, the desired specified relative positioning is maintained upon the application of pressure and rotational forces, in spite of the mentioned continuous lateral opening, without necessitating further stabilising means.

Preferably in the area of these curved portions, recesses on the one hand and tongues on the other hand are provided for securing the cages in their end positions, with tongue and recesses being in a latching or clawing engagement with each other.

In addition, there is the possibility that at least in the area of the curved portions of the opposite surfaces of the cages a preferably punched locking toothing is provided in order to preclude any displacement or undesired rotation of the cages relative to each other.

In the area of the portion of the U-shaped cages, which connects the legs, holes for accommodating a locking screw are arranged, with the corresponding hole of the outer cage comprising a thread.

The height-adjustability of the vertebral implant is realised in a preferred embodiment in that the inner cage, preferably in the area of the portion connecting the legs, comprises a first elongated hole with toothing, which extends in the longitudinal direction, in order to achieve a relative movement and a corresponding adjustment between the cages in cooperation with a set screw.

A further, second elongated hole is preferably provided opposite the first elongated hole and serves to secure the adjusted position by means of the locking screw.

In order to facilitate the penetration of the locking projections until the abutment of the tongue-like vertebral supporting surfaces relative to the neighbouring vertebrae, the locking projections which are, for example, of a triangular shape, are ground to a cutting edge.

The locking projections and vertebral supporting surfaces which are provided at one each of the end faces of the first and second cages, are suitably arranged in an alternating manner in order to ensure the desired planeness.

BRIEF DESCRIPTION OF THE DRAWINGS

In the following, the invention will be explained in more detail with reference to one embodiment illustrated in the figures.

These show:

FIG. 1a a side view of the inner cage of the vertebral implant;

FIG. 1b a side view of the inner cage of the vertebral implant with the opening area being visible;

FIG. 1c a plan view of the inner cage of the vertebral implant;

FIG. 1d a section along line A—A in FIG. 1b;

DESCRIPTION OF THE PREFERRED EMBODIMENTS

Figure 2:
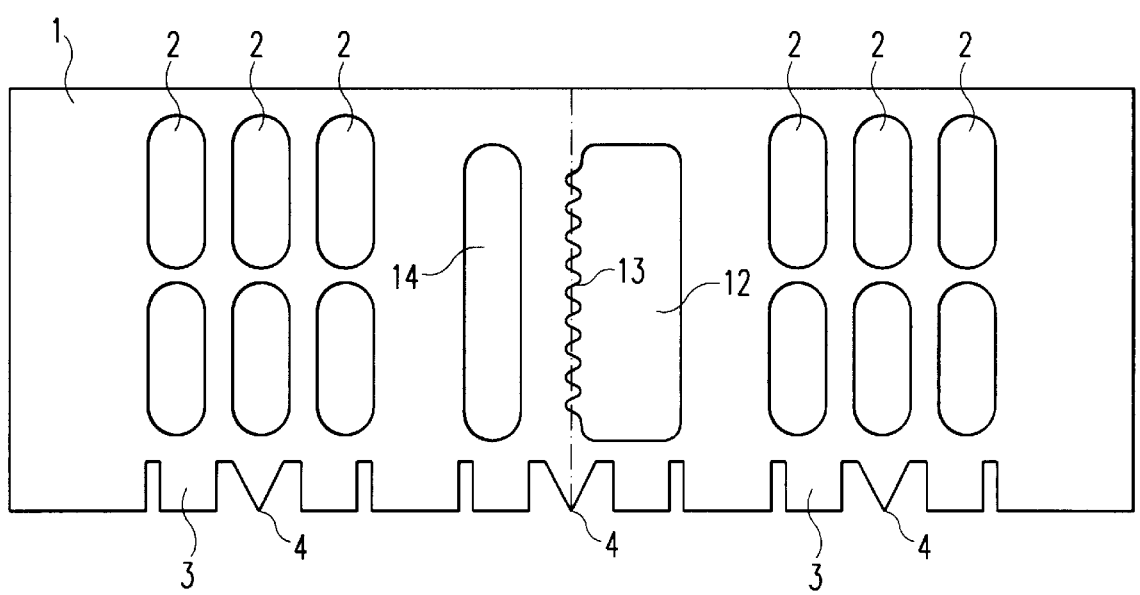
FIG. 2 an illustration of the cutting template for an inner cage of the vertebral implant with the provided toothing of the elongated hole for the continuous height adjustability.

As can be seen from FIG. 1a the inner first cage 1 comprises recesses or holes 2 provided in its legs.

At one end face of the first inner cage 1, angular tongue-like vertebral support surfaces 3 as well as tooth-like locking projections 4 which alternate with these support surfaces 3 and extend in the longitudinal direction are provided. The locking projections can comprise a cutting edge 16 at their tips for facilitating the penetration into the respective, opposite surface of the vertebra.

In an inwardly directed curved portion 5 (see also FIG. 1c) a recess 6 is provided which can be latched or clawed by means of bending with a tongue 7 of the outer cage 8.

As can be seen from FIGS. 1a to 1d, the area and the shape have been optimised in such a manner that, on the one hand, a small metal quantity is used, on the other hand, however, the mechanical stability meets the requirements, in particular the post-operative requirements. The abutment edge 9 which can best be seen in FIGS. 1b and 1c, for example, is provided for an increase in stability.

FIG. 2 shows a cutting template of the first inner cage 1, in which the already prepared surfaces 3 for supporting the vertebrae and the locking projections 4 can be seen.

In the embodiment according to FIG. 2 a first elongated hole 12 with a toothing 13 is formed in the area of the portion 11 connecting the legs 10. A second elongated hole 14 is arranged essentially parallel and neighbouring to the first elongated hole 12 and serves to fix the selected adjusting position by means of a locking screw which is located in a threaded hole of the second outer cage 8.

It should be noted that, although not shown in the drawings, a toothing can be provided in the area of the curved portion at or on the opposite surfaces of the first inner cage 1 and on the second outer cage 8, which prevents an undesired displacement or rotation of the cages relative to one another.

As is apparent, in particular, from the illustration in FIG. 2 the cages can be punched from a metallic strip so that the manufacturing costs as a whole can be kept low. The metallic material used for an embodiment is titanium sheet with a thickness of essentially 1 to 1.5 mm.

Figure 3:
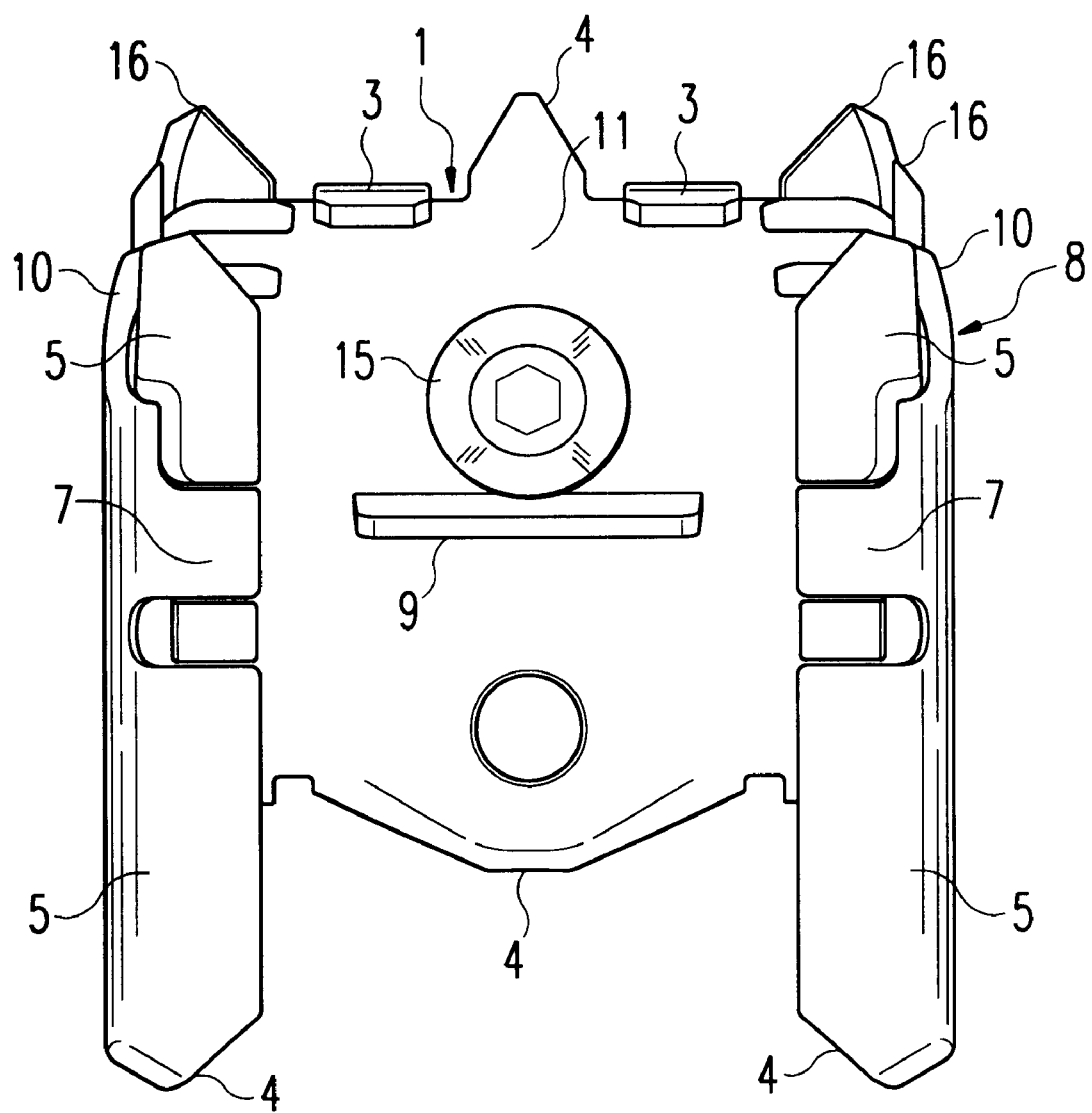
FIG. 3 a perspective illustration of the complete vertebral implant, comprising an inner first cage and an outer second, U-shaped cage.

FIG. 3 shows a vertebral implant ready for transplanting. As can be seen, the first inner cage 1 is encompassed by the second outer cage 8. A locking screw 15 is inserted and can easily be operated from the visible open side. The curved portions 5 of the outer cage 8 show the tongues 7, here in their still non-engaged condition.

The claw engagement is facilitated by means of a forceps-type tool which is inserted into the open area, without undesired transverse forces acting on the implant, which might displace it from its pre-fixed position. The illustration in FIG. 3 also shows the formation of the ground cutting edge 16 at the tooth-like locking projections 4.

The vertebral implant is inserted with the closed side of the cages first, whereupon after the insertion between two slightly spread vertebrae the inner cage 1 is extended and locked. Due to the opening of the legs, there is the possibility to insert and operate the respective locking tools as well as to carry out the filling operation with bone cement or the like in an optimum manner.

In summary, the vertebral implant of the disclosed type allows to reliably support the vertebral column, without the quantity of the foreign matter material which is required for the support exceeding a critical threshold. The handling of the implant itself is uncomplicated and, compared to the state of the art, significantly facilitated due to the height adjustability. The manufacturing costs can be reduced by the configuration of the implant cages guided relative to one another, which are made from metal, preferably titanium sheet by means of punching and bending.

List of Reference Numerals

1 Inner cage
2 Recesses, holes
3 Vertebral supporting face
4 Locking projections
5 Curved portion
6 Recess
7 Tongue
8 Outer cage
9 Abutment edge
10 Legs
11 Connecting portion of legs
12 First elongated hole
13 Toothing
14 Second elongated hole
15 Locking screw
16 Ground cutting edge

What is claimed is:

1. A height-adjustable vertebral implant comprising:

a first, inner U-shaped cage having first legs and a connecting portion connecting the first legs;

a second, outer U-shaped cage having second legs and a connecting portion connecting the second legs;

wherein the second cage is configured to receive the first inner cage and to telescopically guide the first cage;

the first and second legs of the first and second cages aligned with one another such that a continuous lateral opening is defined by the first and second legs;

wherein the first and second cages have a U-shaped end face, respectively, provided with angular, tongue-shaped vertebral supporting surfaces and tooth-shaped projections extending in a longitudinal direction of the first and second cages;

wherein the first and second legs have a free end remote from the connecting portion, respectively, wherein the free ends have an inwardly curved portion, respectively, for strengthening the first and second cages;

wherein the connecting portion of the first cage has a first elongate hole provided with a toothing and extending in the longitudinal direction;

wherein the second cage comprises a set screw engaging the first elongate hole for enabling a relative movement and adjustment between the first and second cages;

wherein the connecting portion of the first cage has a second elongate hole adjacent to the first elongate hole and wherein the second cage comprises a threaded hole;

a locking screw engaging the threaded hole of the second cage and the second elongate hole of the first cage for securing a predetermined end position.

2. The vertebral implant according to claim 1, wherein the curved portions of the first and second cages have facing surface provided with at least one recess on one of the facing surfaces and at least one tongue on the other of the facing surfaces, respectively, wherein the at least one tongue and the at least one recess are configured to engage one another by latching or clawing for securing the first and second cages relative to one another in the predetermined end position.

3. The vertebral implant according to claim 1, wherein the tooth-shaped projections have a cutting edge, respectively, for facilitating penetration into a vertebra.

4. The vertebral implant according to claim 1, wherein the tongue-shaped vertebral supporting surfaces and the tooth-shaped projections alternate.

5. The vertebral implant according to claim 1, wherein the first and second cages are comprised of punched and bent metal.

6. The vertebral implant according to claim 5, wherein the metal is titanium.

7. The vertebral implant according to claim 1, wherein the first and second cages have a polygonal or round or circular or semi-circular cross-section.

8. The vertebral implant according to claim 1, wherein at least the second cage of the first and second cages is provided with holes.

* * * * *